United States Patent [19]

Pavlov et al.

[11] 4,141,925
[45] Feb. 27, 1979

[54] SEPARATING UNEQUALLY SATURATED HYDROCARBONS WITH MONOVALENT COPPER SALT SOLUTIONS IN β-METHOXYPROPIONITRILE

[76] Inventors: Stanislav J. Pavlov, ulitsa Volodarskogo, 15, kv. 46; Valentina A. Stepanova, Uglichskoe shosse, 10, kv. 11; Olga V. Bogdanova, ulitsa Pervomaiskaya, 9, kv. 46; Sergei G. Kuznetsov, ulitsa Sovetskaya, 23/32, kv. 11; Tatyana G. Dorofeeva, Moskovsky prospekt, 82, kv. 87; Alexandr N. Bushin, ulitsa Pervomaiskaya, 9, kv. 21; Gennady A. Stepanov, ulitsa Pervomaiskaya, 9, kv. 3; Leonid K. Eratov, ulitsa Bljukhera, 36, kv. 5; Ariadna B. Kirnos, ulitsa Pervomaiskaya, 9, kv. 5; Boris A. Plechev, prospekt Lenina, 55, kv. 60, all of Yaroslavl; Alexei P. Kharchenko, ulitsa 2 Burovaya, 13, kv. 22; Konstantin N. Bildinov, ulitsa Marshala Rybalko, 96, kv. 37, both of Perm; Oleg P. Yablonsky, Flotsky spusk, 1a, kv. 23; Jury V. Orlov, ulitsa Volkova, 2/4, kv. 2, both of Yaroslavl; Boris E. Ivanov, ulitsa Krasnaya pozitsia, 91, kv. 69, Kazan; Valerian M. Sobolev, naberezhnaya M.Gorkogo, 46/50, kv. 185, Moscow; Mikhail A. Korshunov, ulitsa Pervomaiskaya, 9, kv. 41, Yaroslavl; Svetlana B. Boikova, ulitsa Chkalova, 18, kv. 30, Yaroslavl; Rimma G. Kuzovleva, ulitsa Sverdlova, 23a, kv. 16, Yaroslavl, all of U.S.S.R.

[21] Appl. No.: 731,451

[22] Filed: Oct. 12, 1976

Related U.S. Application Data

[60] Continuation of Ser. No. 630,667, Nov. 10, 1975, abandoned, which is a continuation of Ser. No. 545,713, Jan. 30, 1975, abandoned, which is a division of Ser. No. 228,822, Feb. 24, 1972, abandoned.

[30] Foreign Application Priority Data

Feb. 26, 1971 [SU] U.S.S.R. .............. 1624002
Feb. 26, 1971 [SU] U.S.S.R. .............. 1624003
Feb. 26, 1971 [SU] U.S.S.R. .............. 1626691

[51] Int. Cl.² ............................................. C07C 7/00
[52] U.S. Cl. .................. 260/681.5 C; 260/677 A; 203/51; 203/60; 203/63; 203/61
[58] Field of Search ....................... 203/51, 57–61; 208/308; 260/677 A, 681.5 C

[56] References Cited

U.S. PATENT DOCUMENTS

| | | | |
|---|---|---|---|
| 2,557,923 | 6/1951 | Ray et al. | 260/677 A |
| 3,050,573 | 8/1962 | Anderson et al. | 260/677 A |
| 3,158,555 | 11/1964 | Cornell | 202/39.5 |
| 3,206,377 | 9/1965 | Cornell | 202/39.5 |
| 3,401,112 | 9/1968 | Dunlop et al. | 208/308 |
| 3,449,240 | 6/1969 | Blytas et al. | 208/308 |
| 3,707,575 | 12/1972 | Muller et al. | 260/677 A |
| 3,776,972 | 12/1973 | Tyler | 260/677 A |
| 3,898,135 | 8/1975 | Tidwell et al. | 260/677 A |

*Primary Examiner*—Norman Yudkoff
*Attorney, Agent, or Firm*—Holman & Stern

[57] ABSTRACT

A method of separating proximate boiling-point hydrocarbons using solutions of monovalent copper salts in solvents, said solvents being alkyl-substituted amides and alkyl esters of phosphorus-containing acids having a P═O group, N-alkyl-substituted amides of carboxylic acids, N-alkyl-substituted lactams, dialkyl sulphoxides, alkoxynitriles and N-alkyl-substituted aminonitriles. The method can be used for separating hydrocarbons from small quantities of acetylene compounds and cyclopentadiene.

Large quantities of acetylene compounds are separated from the mixture of proximate boiling-point hydrocarbons by contacting the mixture with said solvents containing no salts of monovalent copper.

5 Claims, 1 Drawing Figure

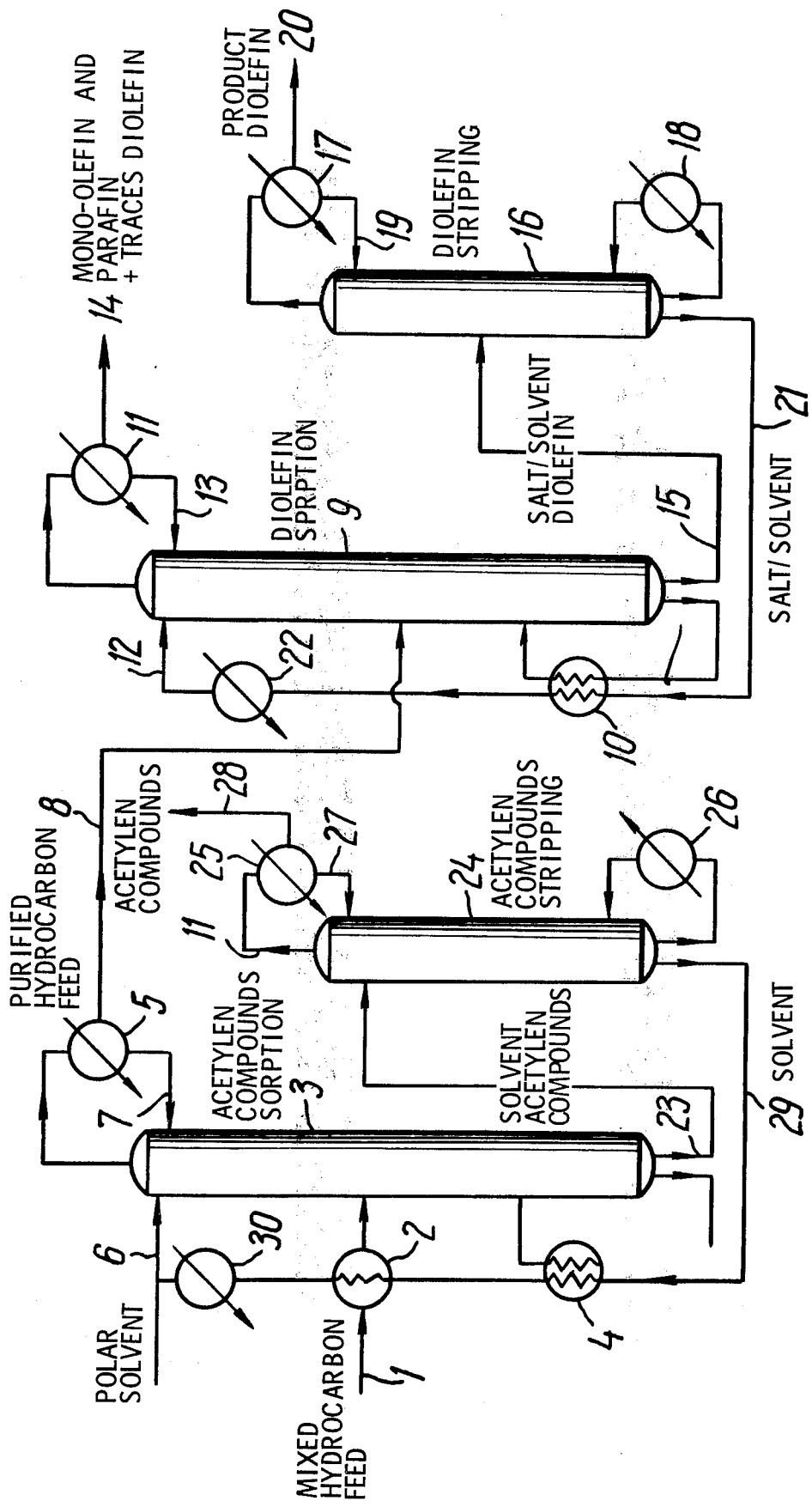

SEPARATING UNEQUALLY SATURATED HYDROCARBONS WITH MONOVALENT COPPER SALT SOLUTIONS IN β-METHOXYPROPIONITRILE

This is a continuation of application Ser. No. 630,667 filed Nov. 10, 1975, which in turn is a continuation of application Ser. No. 545,713, filed Jan. 30, 1975, which in turn is a divisional of Ser. No. 228,822, filed Feb. 24, 1972, all now abandoned.

The present invention relates to processes of separating mixtures of proximate boiling-point hydrocarbons which differ in the number of multiple bonds, and differing multiple bond characteristics and character of multiple bonds character of multiple bonds in their molecules or (and) in the number of substituents at said multiple bond. More particularly, the present invention relates to the separation of mixtures such as alkane-alkene, alkane-alkadiene, alkene-alkadiene, alkane-alkene-alkadiene, n-alkene-isoalkene, n-alkene-isoalkene, n-alkadiene-isoalkadiene.

It is known that effective separation of said mixtures of proximate boiling-point hydrocarbons by using conventional rectification methods often proves to be either impossible or rather costly. For separating hydrocarbons which differ in the number and character of multiple bonds in their molecules extractive rectification with the use of polar organic solvents is the conventional recourse, the most selective of these being acetonitrile, dimethyl formamide, N-methyl pyrrolidone (cf. U.S. Pat. Nos. 2,437,230; 2,396,927; 3,436,436; FRG Pat. No. 1,059,436, etc.).

An inherent disadvantage in the processes of extractive rectification using organic solvents resides in a comparatively low selectivity of the latter when the hydrocarbons to be separated feature different degrees of unsaturation, and in a practically complete absence of selectivity when isomers are to be separated. Thus, for instance, the coefficient of relative volatility of cis-butene-2 and butadiene-1,3 at 50° C. is 1.3 in the case of hydrocarbon having a content of 30% in the most selective organic solvents (acetonitrile, dimethyl formamide, N-methyl pyrrolidone).

For separating said hydrocarbons chemisorption processes are used, such as with water-ammonia solutions of salts of monovalent copper (U.S. Pat. No. 2,375,576 and other). The process of chemisorption with water-ammonia solutions of copper salts, however, is disadvantageous in that hydrocarbons have a relatively low solubility in chemisorption solutions (less than 5 wt.%), a low working temperature (below 0° C) and other difficulties associated with recuperation of the ammonia entrained with the solutions.

To overcome the above-mentioned disadvantages, it was proposed to employ solutions of monovalent copper salts in protogenic organic solvents as the separating agent, e.g., in mixtures of alcohols and amines (U.S. Pat. No. 2,376,239). However, hydroxyl-containing solvents form strong solvates with bivalent copper, enhancing the disproportionation reaction

this resulting in an instability of the solutions.

A more commendable proposal was to use solutions of monovalent copper salts in propionitrile (U.S. Pat. Nos. 3,401,112; 3,449,240. In said Patents acetonitrile is also cited). Propionitrile as a separating agent, however, features a comparatively low boiling point and can easily be entrained by hydrocarbons. However its recuperation from hydrocarbons by washing with water presents difficulties, since propionitrile forms an azeotropic mixture with water when containing 24% of water. Therefore the recuperation of propionitrile from hydrocarbons was proposed to be carried out by extraction with sulpholane (U.S. Pat. No. 3,517,081). It is obvious that the additional step of extraction materially complicates the process and makes it more costly.

It is an object of the present invention to provide an improved method of separating proximate boiling-point hydrocarbons and, more particularly, hydrocarbons differing in the number and character of the multiple bonds in their molecules or (and) in the number of substituents at the multiple bond, which would ensure effective separation of said hydrocarbons without any substantial entrainment of the solvent with the separated hydrocarbons and without having to complicate the system by recuperating the solvent from the separated hydrocarbons.

Another object of the invention is to provide an improved process of separating mixtures of proximate boiling-point hydrocarbons containing a considerable quantity of acetylene compounds.

A further object of the invention is to provide an improved process for separating said hydrocarbons from said small amounts of acetylene hydrocarbons and cyclopentadiene.

These and other objects of this invention will become apparent from the following description thereof.

We have established that separation of proximate boiling-point hydrocarbons which differ in the number and the character of the multiple bonds in their molecules or (and) in the number of multiple bond substitutions can be effectively carried out by using separating agents that are solutions of monovalent copper salts, completely or partially dissociated in an aprotic organic solvents selected from the group consisting of N-alkyl-substituted amides of phosphorus-containing acids having a P=O group, N-alkyl-substituted amides of carboxylic acids, N-alkyl-substituted lactams, dialkyl- sulphoxides, alkoxynitriles, N-alkyl-substituted aminonitriles and esters of phosphorus-containing acids having a P=O group.

The effort in selecting effective solutions of monovalent copper salts in said solvents stems from two consideration the first being the selection of the proper polar organic solvent, and the second the complexation effect resulting from interaction of the hydrocarbons with the ions of the monovalent copper.

The aforesaid solvents feature a high solvating power with respect to the monovalent copper cations and give sufficiently stable solutions for many monovalent copper. Further said solvents do not have an active hydrogen atom, such as —OH, the presence of which would result in high solvating power with respect to the cation of the bivalent copper and, hence, contribute to the disproportionation reaction:

At the same time these solvents are not excessively strong ligands for monovalent copper and therefore they can be substituted by such ligands as alkenes and alkandienes, particularly, alkenes and alkadienes of $C_4$ and $C_5$.

This is an advantage for said solvents over acetonitrile cited as a possible solvent in U.S. Pat. No. 3,401,112, acetonitrile being an excessively strong ligand, in whose solution, as shown hereinbelow, the complexing effect when separating alkenes and alkadienes $C_4 - C_5$ fails to manifest to a sufficient extent.

The boilng points of said solvents are sufficiently high so that they do not form azeotropes with the $C_4-C_5$ hydrocarbons, nor is there required any especially complicated recuperation processes from separated hydrocarbons contrary to the case of recuperation by extraction with sulpholane, as proposed for the propionitrile solvent.

Alkyl groups which substitute hydrogen atoms in the amino and the oxygroups of the proposed solvents may have from one to five carbon atoms.

Most preferable are solvents having methyl and ethyl groups as substituents. Such solvents feature a higher selectivity effect proper than solvents having propyl, butyl and pentyl substituents. Moreover, the above solvents are noted for their higher ionizing effect, and the dissociation of copper salts therein is more complete. The most preferred solvents are phosphoric acid hexamethyltriamide $(CH_3)_6N_3O_3PO$, methylphosphonic acid tetramethyldiamide $(CH_3)_5N_2PO$, dimethylacetamide, N-methyl pyrrolidone, dimethyl sulphoxide, $\beta$-methoxypropionitrile, ethoxypropionitrile, dimethylaminocyan, diethylaminocyan, trimethyl phosphate.

As salts of monovalent copper, various salts can be used which are soluble in the above-cited solvents and at least partially if not completely dissociating in them.

The most preferred salts are those having strong oxygen-containing acids, particularly, cuprous sulphate, cuprous thiosulphate, cuprous sulphite, cuprous nitrate, cuprousbichromate, cuprous chlorate, cuprous phosphate, cuprous trifluoroacetate. Also other readily dissociating salts can be used, such as cuprous tetrafluoroborate, cuprous hexafluorosilicate, and the like.

When said proximate boiling-point hydrocarbons are contacted with the herein-proposed solutions of salts of monovalent copper, absorption of hydrocarbons with a higher degree of unsaturation takes place.

Separation, i.e., desorption of the absorbed hydrocarbons from the separating agent can be effected by various conventional methods, such as by heating, by creating a vacuum, by blowing with an inert gas, particularly with nitrogen or with hydrocarbons, or, else, by extraction with paraffin hydrocarbons.

The desorption of the hydrocarbons from the separating agent may be facilitated by introducing such components into the composition of the latter, which have a higher boiling point than that featured by the hydrocarbons to be separated, but lower than the boiling point of the polar solvent employed; the quantity of these additional components must be such as to ensure a reduction in the boiling point of the separating agent.

Such additives used may be organic substances which, when employed either in their pure form or in combination with solutions of salts of monovalent copper, are not sufficiently active per se for separating said hydrocarbons due to their low ionizing ability. Methyl ethyl ketone, acetone and benzene may be cited as particular examples of such substances.

When said solutions of monovalent copper salts in aprotic solvents are employed for fine purification of hydrocarbons from small quantities of acetylene compounds and cyclopentadiene, the residual amount of acetylene compounds and cyclopentadiene in the thus purified hydrocarbons is not higher than 0.0005%. This figure meets the requirements placed on monomers, e.g., on isoprene and butadiene, which are to be used for stereospecific polymerization in the presence of organometallic catalysts.

Considerable amounts of $\alpha$-acetylene compounds present in the hydrocarbon mixtures to be separated may lead to precipitation of explosion-hazardous cuprous acetylides from said solutions.

We have established that the separation of hydrocarbon mixtures containing large amounts of $\alpha$-acetylene compounds can be effectively carried out in two stages. At the first stage $\alpha$-acetylene compounds are separated by contacting the hydrocarbon mixture with said organic solvents which in this particular case do not contain cuprous salts. The absorbed acetylene compounds are separated from the solvent, and the latter is recycled for further contact with the hydrocarbons.

The hydrocarbons purified from $\alpha$-acetylene compounds are taken, together with a small amount of the solvent, to the second stage, where separation is effected by use of said solutions of monovalent copper salts in said solvents. In order to maintain the required concentration of copper in the solution, a certain portion of the solvent is distilled off and recycled to the first stage. This portion of the solvent usually corresponds to the amount of the solvent which has come, together with the hydrocarbons, to the second stage after the removal of the acetylene compounds therefrom at the first stage.

In a similar manner it is possible to effect the removal of a number of oxygen-, sulphur- and nitrogen-containing compounds together with the $\alpha$-acetylene compounds, the first-mentioned compounds coming into the separation system with the salts of monovalent copper are undesirable, since there may be among them oxidants or ligands stronger than the hydrocarbons being absorbed.

The invention will now be described in greater detail, by way of illustration, with a preferred embodiment of the present method of separation being set forth in the description in conjunction with the accompanying drawing, wherein a typical flow sheet is shown for the case of running the separation process by extractive rectification. The flow sheet as a whole is adapted for separating hydrocarbon mixtures containing considerable quantities of $\alpha$-acetylene compounds. Should the content of the $\alpha$-acetylene compounds in the hydrocarbon mixture be insignificant, the first half of the flow sheet will not be required.

Referring to the drawing, the mixture of hydrocarbons to be separated is first fed via a line 1 into an evaporator 2 and then into the middle portion of an extractive rectification column 3 equipped with a boiler 4 and a partial condenser 5. A polar solvent is first fed into the upper portion of the column 3 via a line 6. The hydrocarbons contacting the solvent results in a separation of acetylene compounds from other hydrocarbons. A fraction is withdrawn from the top of column 3 which is purified from large amounts of acetylene compounds, this fraction being then directed to the condenser 5. The portion of hydrocarbons condensed in the condenser 5 and the solvent entrained therein are returned via a line 7 to the column 3 as a reflux, and the rest of the purified fraction together with the solvent entrained therein is directed via a line 8 to a separation second stage in the form of an extractive rectification column 9 equipped with a boiler 10 and a condenser 11. A separating agent is supplied into the upper portion of the column 9 via a line 12 which is a solution of a salt or of salts of monovalent copper in said polar organic solvent.

From the top of the column 9 the less unsaturated (or less liable to sorption) hydrocarbons are withdrawn and directed to condenser 11 for condensation.

A part of the condensate is returned to the column 9 via line 13 as a reflux, and the rest of the condensate is withdrawn via a line 14 as a ready product. In the boiler 10 the hydrocarbons are partially stripped from the separating agent.

The separating agent with the absorbed more highly unsaturated hydrocarbons is directed from the column 19 via a line 15 to a desorber 16 equipped with a condenser 17 and a boiler 18. The absorbed unsaturated hydrocarbons are stripped from the heated separating agent in the desorber 16 and circulating through boiler 18. The separated hydrocarbon (e.g., butadiene-1,3,isoprene, etc.) is withdrawn from the top of the desorber 16 and directed to the condenser 17 for condensation. A part of the condensate is returned via a line 19 to the desorber 16 are a reflux, and the rest of the condensate is withdrawn via a line 20 as a desired product.

The separating agent free of hydrocarbon is directed from the desorber 16 via a line 21 to the boiler 10 for heat recovery, then it is cooled in a cooler 21 and thence returned to the column 9 via the line 12.

A part of the separating agent is withdrawn from the line 21 for regeneration (from dimers, etc.) (not shown in the drawing). In the process of regeneration, a part of the solvent entrained from the column 3 may be distilled off from the separating agent and returned to line 6 and then to the column 3.

The solvent with the absorbed acetylene hydrocarbons is directed from column 3 via a line 23 to a desorber 24 equipped with a partial condenser 25 and a boiler 26, wherein the main bulk of the acetylene hydrocarbons is stripped off. The condensed solvent and a part of the hydrocarbons are returned from the partial condenser 25 via a line 27 to the desorber 24 as a reflux. The non-condensed acetylene compounds are removed from the system via a line 28.

The solvent freed from the acetylene compounds is directed from the desorber 24 via a line 29 to the boiler 4 and the evaporator 2 for heat recovery; then it is cooled in a cooler 30 and returned to the column 3 via the line 6.

As can be seen from the above-described flow sheet, the herein proposed method is simple and allows for the carrying out of the process without the use of a special solvent recuperation unit. Moreover, the process ensures purification of the hydrocarbons being separated from large quantities of acetylene compounds. The separation of small quantities of acetylene hydrocarbons can be effected by contacting them along with the separating agent in a separate extractive rectification column (not comprised in the flow sheet), followed by desorption thereof.

The processes of extractive rectification and desorption may be recombined in one column. In such a case the withdrawal of the more highly unsaturated hydrocarbons is effected in the vapour phase as a side-draw.

The process may be carried out not only as set forth above, but also in accordance with liquid extraction (liquid-liquid) and counter-current absorption flow methods.

For a better understanding of the present invention specific examples are given hereinbelow for separating proximate boiling-point hydrocarbons.

EXAMPLES 1-3

A mixture of hydrocarbons containing, mainly, $C_4$ (see column 1 of the Table) is contacted with a solution containing a monovalent copper salt in a polar organic solvent.

Coefficients of relative volatility of the hydrocarbons ($\alpha_\infty$) are measured. The values of $\alpha_\infty$ at 50° C at "infinite" dilution with respect to the separating agent are listed in Table 1.

The comparison of the values tabulated for $\alpha_\infty$ shows the selectivity of the proposed separating agents to be essentially superior to that of the pure standard. At the same time, from a comparison of the $\alpha_\infty$ values tabulated in columns 3 and 4 it follows that the solutions of salts of monovalent copper in acetonitrile fail to exhibit any essential complexing effect for the copper ions with hydrocarbons, so that the assertion as to the effectiveness of solutions of acetonitrile containing monovalent copper salts for the separation of hydrocarbons (U.S. Pat. No. 3,401,112) appears to be erroneous.

Therefore not just any organic solvent can be employed to obtain selective solutions of monovalent copper salts.

EXAMPLES 4-5

A mixture of $C_5$ hydrocarbons are contacted with a solution of monovalent copper salt in an organic solvent. The relative volatility coefficients of the hydrocarbons ($\alpha_\infty$) are measured. The values of $E_\infty$ for hydrocarbons at infinite dilution with respect to the separating agent at 50° C. are listed in Table 2 of the specification.

The tabulated values of $\alpha_\infty$ show the selectivity of the hereinproposed separating agents to be considerably higher than that of pure N-methyl pyrrolidone.

EXAMPLES 6-14

A mixture containing two hydrocarbons in a 1:1 ratio is dissolved in a separating agent solution of a monovalent copper salt in a polar organic solvent. The coefficient of relative volatility of the hydrocarbons ($\alpha$) is measured. The values of the coefficients of relative volatility at a temperature of 50° C are listed in Table 3 of the specification.

The tabulated data shows that the solvents proposed herein to be sufficiently selective for separating both hydrocarbons which differ in the number of multiple bonds (cis-butene-2- and butadiene-1,3; 2-methyl-2-butene and isoprene, and the like) and isomers (butene-1 and isobutene).

EXAMPLES 15-17

Solution of monovalent copper salts of different compositions are prepared – both those with and those without adding components featuring boiling points lower than that of a polar solvent and higher than the hydrocarbons to be separated. The boiling points of said solutions are measured at 760 mm Hg. The mixtures of hydrocarbons are contacted with said solutions and the coefficients of relative volatility of the hydrocarbons are measured. The data obtained is listed in Table 4 of the specification.

As can be seen from Table 4, the addition of low-boiling components in an amount from 9 to 12% substantially decreases the boiling point of the separating agent without any material reduction in the selectivity thereof. A reduction in the boiling point of the separating agent is required for diminishing the temperature in the stills of extractive and desorptive rectification columns.

EXAMPLE 18

A $C_4$ fraction of butene dehydrogenation which contains 15% of n-butane, 5% of isobutene, 20% of butene-1, 28% of butane-2 and 32% of butadiene-1,3, is subjected to extractive rectification separation in the presence of an extractant containing 14 wt.% of $Cu_2SO_4$ and 86 wt.% of N-methyl pyrrolidone; with acetylene compounds being absent, only of the second half of the flow sheet represented in the drawing is used.

Separation conditions are as follows:

The temperature of the top of the extractive rectification column 9 is 40° C.; the (internal) reflux ratio is 2.0. The extractant-to-feed ratio is 6:1. The separation results in obtaining butadiene having concentration of 99.5%. The degree of butadiene extraction is 97%.

EXAMPLE 19

A mixture containing 50% of isobutylene and 50% of butene-1 is subjected to separation in column 9 by extractive rectification using a solution containing 20 wt.% of $Cu_2S_2O_3$ in 80 wt.% of dimethyl acetamide.

The separation is carried out on a column having an efficiency of 70 theoretical plates, with the reflux ratio being 12. The result is isobutylene having a concentration of 99%, and butene-1 containing 2.0% of isobutylene. The extractant-to-feed ratio is 15:1.

EXAMPLE 20

A mixture of butene-1, cis-butene-2 and butadiene-1,3 in a weight ratio of 1:1:1 is subjected to separation having an extractive rectification column with a solution of 50 wt.% of $Cu_2SO_4$ in $\beta$-methoxypropionitrile.
  Separation conditions:
  column efficiency, 40 theoretical plates;
  reflux ratio, ca. 2.2;
  temperature, ca. 50° C.
  The extractant-to-feed weight ratio is 8:1.

EXAMPLE 21

Isoprene obtained the dehydrogenation of isopentane which contains 0.016 wt.% of $\alpha$-acetylene compounds (including 0.0005% of 3-methyl-1-butyn, 0.015% of 2-methyl-1-buten-3-yne, 0.0005% of pentyne-1) and 1.1 wt.% of cyclopentadiene was passed through a 0.5 m high packing column filled with 73 g of a solution of 10.4 wt.% $Cu_2SO_4$ in N-methyl pyrrolidone at 75° in order to remove said acetylene compounds and cyclopentadiene therefrom. 16.2 g of isoprene were passed. No $\alpha$-acetylene compounds were traced in the purified isoprene (the sensitivity of the method of analysis for the $\alpha$-acetylene compounds being 0.0002 wt. percent). The purified isoprene had a cyclopentadiene content of 0.3 wt.%.

EXAMPLE 22

An isoamylene-isoprene fraction containing 29.4% of isoprene, 45.3% of isoamylenes, 17.7% of n-amylenes, 2.9% of isopentane, 3.5% of n-pentane, 1.7% of piperylenes, 0.1% of cyclopentadiene and 0.023% of $\alpha$-acetylene compounds was purified from the $\alpha$-acetylene compounds and cyclopentadiene by following the procedure described in Example 21. A solution of 6.2 wt.% $CuNO_3$ in dimethyl acetamide was used as a separation agent taken in an amount of 64 g. 25.3 g of the fraction was passed through the column. No $\alpha$-acetylene compounds were traced in the purified fraction. The cyclopentadiene content was 0.02 wt.%, that of piperylene was 0.6 wt.%.

EXAMPLE 23

Isoprene having a composition similar to that set forth in Example 21 was purified from $\alpha$-acetylene compounds and cyclopentadiene by following the procedure described in Example 21. As a separating agent use was made of a solution of 12.5% $Cu_2SO_3$ in dimethyl sulphoxide taken in an amount of 75 g. 52.3g of isoprene were passed through the column. The content of $\alpha$-acetylene compounds in the purified isoprene was 0.0006 wt.%, that of piperylene, 0.6 wt.%.

EXAMPLE 24

A fraction of hydrocarbons $C_4$ produced by pyrolysis of gasoline and containing 30.5% of butadiene, 30.4% of isobutylene, 24.8% of n-butylenes, 9.9% of n-butane, 4.4% of isobutane, 0.3% of $\alpha$-acetylene compounds (including 0.21% of butenyne, 0.01% of propyne, 0.08% of butyne-1) was purified from the $\alpha$-acetylene compounds by following the procedure described in Example 21. As a purifying (separating) agent use was made of a solution of 15.3 wt.% $Cu_2S_2O_3$ in $\beta$-methoxypropionitrile taken in an amount of 65 g. 78 g of the $C_4$ fraction were passed through the column. In the purified fraction the content of the $\alpha$-acetylene compounds was 0.001 wt.%.

EXAMPLE 25

Isoprene containing 0.016% of $\alpha$-acetylene compounds, 0.5% of cyclopentadiene and 1.0% of piperylene was subjected to purification from said $\alpha$-acetylene compounds and cyclopentadiene by extractive rectification utilizing a solution having 13.7 wt.% $Cu_2SO_4$ in phosphoric acid hexamethyl triamide.
  Separation conditions:
  efficiency of extractive rectification column, 50 theoretical plates;
  pressure, 1 atm;
  temperature, 70° C.;
  reflux ratio, 2;
  extractant-to-feed weight ratio, 10:1

No $\alpha$-acetylene compounds were found in the purified isoprene; that of cyclopentadiene and piperylene therein was 0.0005 and 0.2 wt.%, respectively.

EXAMPLE 26

A $C_4$ fraction produced by oxidative dehydrogenation of butane with iodine said fraction containing 2.2% of butane, 2% of butene-1, 2% of trans-butene-2, 1.5% of cis-butene-2, 69% of butadiene-1,3, 0.1% of butyne-1, 2% of butenyne, 0.1% of butyne-2, 0.1% of oxygen- and sulphur-containing compounds is subjected to separation with the object of obtaining butadiene-1,3.

The separation is carried out in two stages (reference is made to the accompanying drawing). At the first stage including the extractive rectification column 3 and the desorber 24, the $C_4$ fraction is purified from acetylene compounds (mainly from butenyne) and also from the oxygen- and sulphur-containing admixtures. The solvent used in the column 3 is dimethyl acetamide.
  Separation conditions:

temperature of column 3 top, 40° C.;
reflux ratio, 0.8;
solvent-to-feed weight ratio, 1.7:1.

The resulting fraction contains not more than 0.01% of acetylene compounds.

The purified fraction is transfered to column 9 for the second separation stage wherein the separation of butadiene-1,3 is effected. A 5% solution of $CuNO_3$ in dimethyl acetamide is used as the separating agent.

Separation conditions:
Temperature of column 9 top, 40° C.;
reflux ratio (internal), 5;
separating agent-to-feed ratio, 6:1

99.5% butadiene is obtained. The degree of butadiene extraction is 97% pure.

EXAMPLE 27

A $C_5$ fraction obtained by pyrolysis of gasoline which contains 16% of isopentane, 16% of n-pentane, 18% of isoamylenes, 20% of isoprene, 10% of piperylene, 1.5% of cyclopentadiene, 0.08% of pentyne-1 and 0.2% of 2-methyl-1-buten-3-yne (isopentenyne) is subjected to extraction for separation of the diolefine fraction. The separation is carried out in two stages, in accordance with the flow sheet shown in the drawing. In the first stage including the extractive rectification column 3 and the desorber 24 the $C_5$ fraction is purified from acetylene compounds (mainly from 2-methyl-1-buten-3-yne). N-methyl pyrrolidone was used as the solvent.

Purification conditions:
temperature of column 3 top, 40° C.;
reflux ratio, 1.0;
solvent-to-feed weight ratio, 2:1.

The resulting $C_5$ fraction which contains not more than 0.01% of acetylene hydrocarbons (including not more than 0.008% of 2-methyl-1-buten-3-yne) is directed to the second stage for separation, with the second stage including the extractive rectification column 9 and the desorber 16. The separation of the hydrocarbons is effected in column 9. A 15% solution of $Cu_2SO_4$ in N-methyl pyrrolidone was used as the separating agent.

Separation conditions:
Temperature of column 9 top, 40° C.;
reflux ratio (internal), 2;
separating agent-to-feed weight ratio, 8:1.

The fraction thus obtained contains 99.5 wt.% of diolefines $C_5$.

Table 1

| Name of hydro carbons | $\alpha^*$ elasticity of vapours of pure hydrocarbons | $\alpha^\infty$ in presence of acetonitrile (without salt) with respect to butadiene | $\alpha^\infty$ in presence of 10 wt. % $Cu_2SO_4$ in acetonitrile | Example 1 In presence of solution of 5 wt. % CuCl in phosphoric acid hexamethyl triamide | | Example 2 In presence of solution of 50 wt. % $Cu_2SO_4$ in β-methoxypropionitrile | | Example 3 In presence of 8.7 wt. % $Cu_2SO_4$ in methyl ester of methylphosphini acid |
|---|---|---|---|---|---|---|---|---|
| | | | | with respect to butadiene-1,3 | with respect to isobutene | with respect to butadiene-1,3 | with respect to isobutene | with respect to butadiene-1,3 |
| 1 | 2 | 3 | 4 | 5 | 6 | 7 | 8 | 9 |
| Propane | 3.01134 | — | — | 15.17 | 4.76 | 22.35 | 414 | — |
| Isobutane | 1.189 | 4.18 | 4.21 | 7.82 | 2.45 | 9.64 | 1.78 | — |
| Propene | 3.594 | — | — | 6.45 | 2.02 | 8.21 | 1.52 | 11.34 |
| n-Butane | 0.869 | 2.960 | 3.02 | 5.43 | 1.700 | 7.6 | 1.41 | 4.98 |
| Isobutene | 1.060 | 1.950 | 1.96 | 3.18 | 1.00 | 5.4 | 1.0 | 2.96 |
| Butene-1 | 1.053 | 1.950 | 1.96 | 1.94 | 0.609 | 3.00 | 0.56 | 2.96 |
| Trans-Butene-2 | 0.842 | 1.66 | 1.69 | 2.85 | 0.895 | 2.91 | 0.54 | 2.63 |
| cis-Butene-2 | 0.785 | 1.45 | 1.495 | 2.37 | 0.740 | 2.75 | 0.51 | 2.12 |
| Butadiene-1,3 | 1.00 | 1.00 | 1.00 | 1.0 | 0.310 | 1.00 | 0.18 | 1.00 |
| Allene | 2.765 | 2.03 | 2.01 | 0.76 | 0.240 | 0.63 | 0.12 | — |
| Methyl allene | 0.639 | 0.76 | 0.75 | 0.446 | 0.14 | 0.389 | 0.07 | 0.564 |
| Butenyne | 0.787 | 0.39 | — | less than 0.1 | less than 0.1 | less than 0.1 | less than 0.1 | less than 0.1 |
| Propyne | 1.996 | 0.99 | — | | | | | |
| Butyne-1 | 0.548 | 0.47 | — | | | | | |
| Butyne-2 | 0.383 | 0.29 | — | 0.323 | 0.101 | 0.267 | 0.05 | 0.364 |

Table 2

| Name of hydrocarbon | $\alpha^*$-elasticity of vapours of pure hydrocarbons | $\alpha^\infty$ in presence of pure N-methyl pyrrolidone | Example 4 $\alpha^\infty$ in presence of solution of 12% $Cu_2SO_4$ in N-methyl pyrrolidone | Example 5 $\alpha^\infty$ in presence of solution of 43% $CuS_2O_3$, in phosphoric acid hexamethyl triamide |
|---|---|---|---|---|
| | with respect to isoprene | | with respect to isoprene | |
| 1 | 2 | 3 | 4 | 5 |
| Isopentane | 1.204 | 4.69 | 8.45 | 19.5 |
| 3-Methyl-1-butene | 1.536 | 3.47 | 3.61 | 3.3 |
| 2-Methyl-1-butene | 1.099 | 2.18 | 2.85 | 4.24 |
| 2-Methyl-2-butene | 0.867 | 1.75 | 2.61 | 5.83 |
| Isoprene | 1.0 | 1.0 | 1.0 | 1.0 |
| trans-1,3-Pentadiene | 0.774 | 0.77 | 0.80 | 0.85 |
| Cyclopentadiene | 0.807 | 0.545 | 0.79 | — |
| cis-1,3-Pentadiene | 0.725 | 0.70 | 0.60 | 0.67 |
| 2-Pentyne | 0.482 | 0.46 | 0.50 | |
| 3,3-Dimethylbutyne | 0.937 | 0.83 | less than 0.1 | less than 0 |
| Pentyne-1 | 0.838 | 0.46 | less than 0.1 | less than 0.1 |
| 2-Methyl-1-buten-3-yne | 1.049 | 0.5 | less than 0.1 | less than 0.1 |

Table 3

| Example No. 1 | Hydrocarbons to be separated 2 | Relative elasiticity of vapours of pure hydrocarbons 3 | Separating agent 4 | Content of salt in solution, wt. % 5 | Content of hydrocarbons in separating agent 6 | α-coefficient of relative volatility of hydrocarbons in presence of separating agent 7 |
|---|---|---|---|---|---|---|
| 6 | cis-Butene-2 & butadiene-1,3 | 0.78 | $Cu_3(PO_4)$ in β-methoxypropionitrile | 45.2 | 15 | 1.59 |
| 7 | 2-Methyl-2-butene & isoprene | 0.87 | $Cu_2S_2O_3$ in phosphoric acid hexamethyl triamide | 20.0 | 15 | 2.1 |
| 8 | 2-Methyl-2-butene and isoprene | 0.87 | $Cu(CF_3COO)$ in β-methoxypropionitrile | 22.4 | 15 | 1.65 |
| 9 | 2-Methyl-2-butene and isoprene | 0.87 | $Cu(CF_3COO)$ in diethylcyanamide | 15.0 | 10 | 1.59 |
| 10 | 2-Methyl-2-butene and isoprene | " | $CuNO_3$ in methylphosphinic acid methyl ester | 7.4 | 15 | 1.56 |
| 11 | isobutene & Butene-2 | 1.0 | $Cu_2SO_3$ in β-methoxypropionitrile | 41.5 | 12 | 1.19 |
| 12 | Isobutene & butene-2 | 1.0 | $CuNO_3$ in phosphoric acid hexamethyl triamide | 20.0 | 10 | 1.23 |
| 13. | 1-Pentene & cis-1,3-pentadiene (piperylene) | 1.57 | $Cu(CF_3COO)$ in phosphoric acid trimethyl ester | 15.0 | 15 | 3.73 |
| 14. | cis-Butene-2 & butadiene-1.3 | 0.78 | $Cu_2BF_4$ in N-methyl pyrrolidone | 10.0 | 15 | 2.0 |

Table 4

| Example No. 1 | Solvent and its content, wt. % 2 | Copper salt and its content, wt. % 3 | Additive for reducing boiling point, wt. % 4 | Boiling point of solutions at 760 mm Hg °C. 5 | Hydrocarbons being separated 6 | $α^∞$ in presence of separating agent 7 |
|---|---|---|---|---|---|---|
| | N-methyl pyrrolidone, 89% | $Cu_2SO_4$ 11% | — | >200 | isobutene & butene-2 | 1.65 |
| | acetone, 99.2% | $Cu_2SO_4$, 0,8% (limit of solubility) | | 58 | Isobutene & butene-2 | not selective |
| 15 | N-methyl pyrrolidone, 79% | $Cu_2SO_4$ 11% | acetone, 10% | 125 | Isobutene & butene-2 | 1.4 |
| | Phosphoric acid hexamethyl triamide, 80% | $Cu_2SO_4$, 20% | — | >250 | 2-methyl-2-butene & isoprene | 2.4 |
| | methyl ethyl ketone, 97.5% | $Cu_2SO_4$, 2.5% (limit of solub.) | — | 80.1 | 2-methyl-2-butene and isoprene | 1.23 |
| 16 | Phosphoric acid hexamethyl triamide, 68% | $Cu_2SO_4$, 20% | methyl ethyl ketone, 12% | 137 | 2-Methyl 2-butene | 2.0 |
| | N-methyl pyrrolidone, 89% | $Cu_2SO_4$,11% | | 200 | cis-butene-2 & butadiene-1,3 | 2.8 |
| | Benzene, 98% | $Cu_2SO_4$, 2% (limit of solub.) | — | 85 | cis-butene-2 & butadiene | not selective |
| 17 | N-methyl-pyrrolidone 80% | $Cu_2SO_4$, 11% | benzene, 9% | 145 | cis-butene-2 and butadiene 1,3 | 2 |

We claim:

1. A method of separating mixtures of unequally saturated $C_4$-$C_5$ hydrocarbons comprising the steps of:
   contacting said mixtures with a separating agent, said separating agent being a solution of salts of monovalent copper of oxygen-containing acids partially or completely dissociated in β-methoxypropionitrile, whereupon the $C_4$-$C_5$ hydrocarbons that are more highly unsaturated are selectively absorbed forming an intermediate solution;
   physically separating the less highly unsaturated hydrocarbon from the intermediate solution; and
   desorbing said separating agent from said intermediate solution to release the more highly unsaturated $C_4$-$C_5$ hydrocarbons.

2. The method of claim 1, wherein butane, butenes and butadiene are separated.

3. The method of claim 1, wherein isopentane, isopentenes and isoprene are separated.

4. The method of claim 1, wherein acetylene compounds and cyclopentadiene are present in said mixtures, said acetylene compounds and cyclopentadiene being absorbed with the more highly unsaturated $C_4$-$C_5$ hydrocarbons into the intermediate solution comprising the further step of
   separating the acetylene compounds and cyclopentadiene from the separating agent after the more highly unsaturated $C_4$-$C_5$ hydrocarbons have been removed from the intermediate solution.

5. The method as claimed in claim 1, wherein n-butene and isobutene are separated.

* * * * *